US009386923B2

(12) United States Patent
Winter et al.

(10) Patent No.: US 9,386,923 B2
(45) Date of Patent: Jul. 12, 2016

(54) SYSTEM AND METHOD FOR AUTOMATIC SENSOR POSITION RECOGNITION

(75) Inventors: Stefan Winter, Aachen (DE); Juergen Te Vrugt, Aachen (DE); Richard Daniel Willmann, Siegburg (DE); Gerd Lanfermann, Aachen (DE); Edwin Gerardus Johannus Maria Bongers, Eindhoven (NL)

(73) Assignee: Koninklijke Philips N.V., Eindhoven (NL)

( * ) Notice: Subject to any disclaimer, the term of this patent is extended or adjusted under 35 U.S.C. 154(b) by 536 days.

(21) Appl. No.: 12/669,841

(22) PCT Filed: Jul. 22, 2008

(86) PCT No.: PCT/IB2008/052940
§ 371 (c)(1),
(2), (4) Date: Jan. 20, 2010

(87) PCT Pub. No.: WO2009/013708
PCT Pub. Date: Jan. 29, 2009

(65) Prior Publication Data
US 2010/0188231 A1      Jul. 29, 2010

(30) Foreign Application Priority Data

Jul. 26, 2007  (EP) .................................... 07113175

(51) Int. Cl.
*G08B 23/00*      (2006.01)
*A61B 5/00*       (2006.01)
(Continued)

(52) U.S. Cl.
CPC . *A61B 5/00* (2013.01); *A61B 5/061* (2013.01); *A61B 19/44* (2013.01); *A61B 5/0402* (2013.01);
(Continued)

(58) Field of Classification Search
CPC .......... G06K 17/00; G06K 2017/0045; G06K 2017/0051; G06K 2017/0074; G06K 7/10336; G08B 13/2462; A61B 5/064; A61B 5/065; A61B 5/066; A61B 5/6813; A61B 5/684; A61B 5/7271
USPC .............. 340/573.1, 686.1, 686.6, 10.1, 10.4, 340/10.42, 10.5, 10.52, 12.52, 572.1–572.9
See application file for complete search history.

(56) References Cited

U.S. PATENT DOCUMENTS

| | | | |
|---|---|---|---|
| 6,047,203 | A | 4/2000 | Sackner et al. |
| 6,070,269 | A | 6/2000 | Tardif et al. |

(Continued)

FOREIGN PATENT DOCUMENTS

| | | |
|---|---|---|
| DE | 10337235 | 3/2005 |
| JP | H04303416 A | 10/1992 |

(Continued)

*Primary Examiner* — Steven Lim
*Assistant Examiner* — Mancil Littlejohn, Jr.

(57) ABSTRACT

An automatic sensor position recognition system including a position recognition unit located at pre-determined positions on a person's body and bearing a unique identification; a sensor bearing a unique identification; a communication unit assigned to the sensor and being in communication with the position recognition unit and the sensor; a data processing unit in communication with the communication unit; and a database being in communication with the data processing system and comprising the correlation of the unique identification of the position recognition unit and the pre-determined position of the position recognition unit. The system provides an automatic association between sensors and body segments as well as means to obtain these associations.

12 Claims, 1 Drawing Sheet

(51) Int. Cl.
*A61B 5/06* (2006.01)
*A61B 19/00* (2006.01)
*A61B 5/0402* (2006.01)
*A61B 5/0488* (2006.01)
*A61B 5/11* (2006.01)

(52) U.S. Cl.
CPC ............. *A61B 5/0488* (2013.01); *A61B 5/11* (2013.01); *A61B 2019/442* (2013.01); *A61B 2019/448* (2013.01); *A61B 2019/545* (2013.01)

(56) References Cited

U.S. PATENT DOCUMENTS

| | | | |
|---|---|---|---|
| 6,496,705 B1* | 12/2002 | Ng et al. | 455/502 |
| 6,687,523 B1 | 2/2004 | Jayaramen et al. | |
| 6,720,888 B2* | 4/2004 | Eagleson et al. | 340/905 |
| 6,755,795 B2 | 6/2004 | Marmaropoulos et al. | |
| 6,860,422 B2* | 3/2005 | Hull et al. | 235/376 |
| 6,970,731 B1 | 11/2005 | Jayaraman et al. | |
| 7,004,910 B2* | 2/2006 | Lindsey | 600/549 |
| 7,173,437 B2* | 2/2007 | Hervieux et al. | 324/663 |
| 7,357,308 B2* | 4/2008 | Matz | 235/380 |
| 7,388,494 B2* | 6/2008 | Campagna | 340/572.1 |
| 7,489,806 B2 | 2/2009 | Mohri et al. | |
| 7,850,912 B2* | 12/2010 | Favuzzi et al. | 422/63 |
| 7,969,307 B2* | 6/2011 | Peeters | 340/572.1 |
| 2004/0053444 A1 | 3/2004 | Yoneda et al. | |
| 2004/0174261 A1* | 9/2004 | Volpi et al. | 340/572.1 |
| 2004/0178270 A1* | 9/2004 | Pradhan et al. | 235/462.13 |
| 2004/0262377 A1 | 12/2004 | Matz | |
| 2005/0034485 A1 | 2/2005 | Klefstad-Sillonville et al. | |
| 2005/0137464 A1* | 6/2005 | Bomba | 600/300 |
| 2005/0194012 A1 | 9/2005 | Ito et al. | |
| 2005/0275416 A1* | 12/2005 | Hervieux et al. | 324/663 |
| 2006/0066449 A1* | 3/2006 | Johnson | 340/539.12 |
| 2006/0235328 A1 | 10/2006 | Willis | |
| 2006/0242293 A1* | 10/2006 | Russ | 709/224 |
| 2006/0282021 A1 | 12/2006 | DeVaul et al. | |
| 2008/0281234 A1 | 11/2008 | Goris et al. | |

FOREIGN PATENT DOCUMENTS

| | | |
|---|---|---|
| WO | WO0067633 | 5/2000 |
| WO | WO0105297 | 1/2001 |
| WO | WO2004017831 | 3/2004 |
| WO | WO2004069048 | 8/2004 |
| WO | WO2005011488 | 2/2005 |
| WO | WO2005089645 | 9/2005 |
| WO | WO2006000345 | 1/2006 |
| WO | WO2006082565 | 8/2006 |
| WO | WO2007070997 | 6/2007 |

\* cited by examiner

SYSTEM AND METHOD FOR AUTOMATIC SENSOR POSITION RECOGNITION

BACKGROUND OF THE INVENTION

The present invention concerns an automatic sensor position recognition system. The present invention also concerns a method for automatically recognizing the position of a sensor on a person's body and the use of such a system.

Upper and lower limb impairments are among the most common forms of neurological deficits after a stroke. Patients suffer from insufficient coordination capabilities and weak muscles. Other conditions that may be treated are cognitive defects, vision impairments and speech problems. Some of the relevant therapeutic procedures can be executed at home, under remote supervision.

In order to evaluate the motor performance of the patient and provide appropriate feedback, data about the patient's movements are required. To this end, sensors or markers are attached to the patient's body at different locations. While the absolute orientation of the sensors or markers that are used can be determined, their absolute position in space cannot be determined. For transforming the orientation measurements into body movements and postures it is therefore necessary to know the body segment which a sensor is attached to.

Currently, this information is provided manually to a data processing unit by associating the body segment with the unique sensor identification. This procedure is always required when the sensors are attached to the body. Since it requires human interaction it is not only error-prone but is also an obstacle particularly for impaired patients when using such a system.

WO 2004/053444 discloses a system and method for monitoring the body temperature of a person. The system comprises one or more sensor devices, where each sensor device is capable of measuring a temperature at a known location of a body of a human or other animal. Each sensor transmits a temperature measurement value and sensor identification to a monitor device. The monitor device receives the temperature measurement value and sensor identification, and computes an adjusted temperature value based upon the position of the measuring sensor, body age, and time of age. As the sensors report a different temperature depending on their location on the body, the importance of assigning a measured temperature to an individual sensor is stated. This is undertaken using a sensor registration table comprising a sensor identification number, a unique sensor registration number assigned during sensor manufacture, a sensor position indicator, body age, and upper and lower alarm limits. Thus, the information has to be entered manually with the associated drawbacks.

From the above it is apparent that a need still exists in the art for an automatic sensor position system and a method for automatically recognizing the position of a sensor on a person's body.

SUMMARY OF THE INVENTION

The present invention addresses this and other needs by providing an automatic sensor position recognition system comprising:
- a position recognition unit located at pre-determined positions on a person's body and bearing a unique identification;
- a sensor bearing a unique identification;
- a communication unit assigned to the sensor and being in communication with the position recognition unit and the sensor;
- a data processing unit in communication with the communication unit; and
- a database being in communication with the data processing system and comprising the correlation of the unique identification of the position recognition unit and the pre-determined position of the position recognition unit.

The position recognition unit is to be understood as a device or a marking that is located at a pre-determined position on a person's body. It bears a unique identification that can be read by other devices. This identification can be in the form of a binary, decimal, hexadecimal or otherwise expressed number, alphanumeric characters, graphical symbols and the like. The uniqueness relates to the fact that no other unit within the system bears the same identification. The identification can also be selected in such a way that the identification is unique for all units ever manufactured, for example by expressing the identification in a 32 bit or 64 bit binary number. The pre-determined position of the unit can be a location such as the person's head, upper arm, lower arm, shoulder, finger, hand, torso, thigh, lower leg or foot.

The sensor whose position is to be recognized automatically also bears a unique identification. This identification can be in the form of a binary, decimal, hexadecimal or otherwise expressed number, alphanumeric characters, graphical symbols and the like. The uniqueness relates to the fact that no other sensor within the system bears the same identification. The identification can also be selected in such a way that the identification is unique for all such sensors ever manufactured, for example by expressing the identification in a 32 bit or 64 bit binary number The communication unit is assigned to the sensor in a logical and/or in a physical way. When it is assigned in a logical way then the communication unit is identifiable as belonging to a certain sensor. It can also be assigned to the sensor physically, for example by being integrated into the sensor. Firstly, the communication unit can transmit the unique sensor identification and the sensor signals to a data processing unit so the sensor signals can be further processed and evaluated. Secondly, the communication unit can read the unique identification of the position recognition unit. In combination, the communication can thus transmit both unique identifications associated with each other. The transmission can be undertaken via a wired connection, by wireless techniques such as infrared, bluetooth, IEEE 802.11 and the like or by using the conductivity of the human body. An example of the latter would be transmitting electrical signals via the skin of a person. This body-coupled communication has the advantage of allowing a great freedom of movement for the person. For the case that the sensor, the communication unit and the data processing unit are all placed on the person's body it is also possible to incorporate them into a body area network. The individual components of the body area network may communicate by the techniques as mentioned above.

The data processing unit receives signals from the communication unit. Additionally, it may directly receive signals from the sensor. It is in communication with a database. This database has information stored about which position recognition units are meant to be at which pre-determined positions. This is undertaken by way of correlating the unique identification of the position recognition unit and its pre-determined position.

Thus, when placing the communication unit with the sensor on the position recognition unit, the unique identifiers of the of the sensor and the position recognition unit are paired and transmitted to the data processing unit.

The database may be a separate physical entity or a logical entity. As a separate physical entity the database may reside on its own mass storage device and be connected to the data processing unit via an interface. As a logical entity it may be split up and have its individual components integrated into the position recognition unit and/or sensor. In this form the unique identifier of the position recognition unit also comprises information about where the position recognition unit is located. The communication of the logical database with the data processing unit is also effected via the communication unit.

Accessing the database then provides all information needed to assign a position on the person's body to the sensor in question. The data processing unit can then, for example, calculate a correct representation of the person in form of an avatar.

It is also possible to sense when a sensor has been removed from the position recognition unit. This task can be performed by the communication unit. In order to keep the data pair correlation up to date the system can then register that the specific sensor is not present anymore. The same applies to the situation when the sensor is switched off or stops transmitting measurements, which allows for error correction.

In summary, the system according to the invention provides an automatic association between sensors and body segments as well as means to obtain these associations. As a result, no human interaction is required any more to assign a body segment to a sensor. Thus, assignment errors can be prevented and the patient is not burdened any more with attaching a particular sensor to a specific body segment and can concentrate more on the exercises he is supposed to undertake or, in the case of body temperature measurement, can be more assured that the temperature readings from different sensors are interpreted correctly. This is especially the case for when new sensors are introduced, either as a replacement for old sensors or as an addition to the system.

DETAILED DESCRIPTION OF THE INVENTION

Before the invention is described in detail, it is to be understood that this invention is not limited to the particular component parts of the devices described or process steps of the methods described as such devices and methods may vary. It is also to be understood that the terminology used herein is for purposes of describing particular embodiments only, and is not intended to be limiting. It must be noted that, as used in the specification and the appended claims, the singular forms "a," "an" and "the" include singular and/or plural referents unless the context clearly dictates otherwise. Thus, for example, reference to "a sensor" includes two or more sensors, reference to "a position recognition unit" includes more than one such devices, and the like.

In one embodiment of the present invention the unique identification information of the position recognition unit is stored in a form that is readable by optical means. Examples for such a storage form include bar codes and two-dimensional pixel array. Preferably, these markings are scanned via a laser beam. Advantages of optical reading of the identification include the low cost of deploying the information as it can be simply achieved by using printed stickers. Thus, in its simplest form, the position recognition unit is a bar code label.

In another embodiment of the present invention the unique identification information of the position recognition unit is stored in a form that is readable by electrical or electronic means. Examples for this include wireless transmissions such as radio frequency identification (RFID) and wired means where the position recognition unit bears electrical contacts that have to be touched by the correct contacts of the communication unit in order to read out the identification. Advantages of electrical reading include the possibility of conveying a great amount of data and, in the case of RFID, that reading is not hampered when the position recognition unit is concealed beneath clothing.

In another embodiment of the present invention the position recognition unit is part of a garment worn by the person. Examples include jackets, pants and belts where the position recognition unit is placed. Furthermore, the garment may be tailored to only permit wearing it in one certain way. An example would be a glove, a sock or a garment worn over the shoulder and the upper arm. This specific tailoring serves to restrict the location of the position recognition unit. Optical markings, RFID chips and other means for storing information can be placed on or in the garment. In addition, the sensors can then be fastened to the garment by placing them into pockets. The position recognition units could also then be integrated into the pockets. Advantages of placing the position recognition units in a garment as mentioned above include that the person only needs to carry the units when needed.

In another embodiment of the present invention the position recognition unit is located directly on and/or in the person's body. For example, RFID chips may be glued to the skin or implanted under the skin. Likewise, optical markings may be applied directly to the skin with permanent or non-permanent ink. This includes tattooing the optical markings. In this context, non-permanent ink is an ink that is degraded or washes off after a time period of, for example, 4 weeks, 8 weeks, 12 weeks or one year. Reversible addition of the position recognition units provides for that they need not be worn any more when the person does not need to perform exercises any more. The advantage of attaching position recognition units directly to the person's body is that their position can be very well-defined and non-changing. Furthermore, this simplifies affixing a sensor to the person's body. For example, a sensor must only be strapped to the respective limb without being worn in a special suit.

In a further embodiment of the present invention the position recognition unit and the sensor are adapted to interact in such a way that the reading of the unique identification information of the position recognition unit is permitted in only one pre-defined spatial orientation of the sensor. This serves to confine the sensor if there are several possible ways of placing it on the person's body. For example, it can be excluded that a sensor is placed upside down on the person. Ways for achieving such a restriction include unsymmetrically placed electrical contacts on the position recognition unit that are matched on the side of the communication unit and unsymmetrically placed optical marks. Likewise, the position recognition unit may also comprise mechanical elements that restrict attaching the communication unit to one spatial orientation. By permitting the reading of the unique identification information only in one pre-defined spatial orientation it is also possible to determine the orientation and exact relative position of the sensor with respect to the person's body part in question. For example, in the case of a bar code optical marking it may be determined in which direction the lines of the bar code run. From this the orientation of the sensor may be determined. Likewise, failure to position the sensor correctly may be communicated to the user by means such as optical, electrical or tactile feedback.

In another embodiment of the present invention the sensor is selected from the group comprising motion sensors, inertial sensors, acceleration sensors, gravity sensors, magnetic field sensors, body temperature sensors, pulse sensors, blood oxygen sensors, electromyographical sensors, electrocardiographical sensors and/or optical markings for visual tracking. These types of sensors are advantageously used for monitoring the body stance, motion or condition of a person. Several sensors may be combined, for example acceleration sensors and gravity sensors. Body temperature sensors may be employed to monitor a fever of a person or the person's physical exertion. Electromyographical sensors can be used to assess the level of fatigue of a certain limb or body segment. For example, uneven distribution of fatigue between the two legs of a person may indicate that the person is overexerting one leg and thus not walking correctly. As electrocardiographical sensors need to be placed correctly on various locations of a patient's body, such as chest, arms and legs, they also benefit from being incorporated into a system according to the present invention. Optical markings for visual tracking are also advantageously employed. They can be identified by a camera in order to represent the stance or motion of a person.

The present invention is further concerned with a method for automatically recognizing the position of a sensor on a person's body comprising the steps of:
  providing a position recognition unit at a pre-determined position on a person's body, the position recognition unit bearing a unique identification;
  placing a sensor onto the position recognition unit;
  reading the unique identification from the position recognition unit using a communication unit assigned to the sensor;
  reading the unique identification of the sensor;
  transmitting the data pair of the unique identifications of the position recognition unit and the sensor to a data processing unit;
  accessing a database comprising the correlation of the unique identification of the position recognition unit and the pre-determined position of the position recognition unit; and
  correlating the unique identifier of the sensor with the pre-determined position of the position recognizing unit.

In the initial step a uniquely identifiable position recognition unit is placed on the person's body in a pre-defined location. This can be either directly on the body or by means of a garment worn by the person. This position and the unique identification of the position recognition unit are correlated and stored in a database. Examples of such database entries could be:
position recognition unit #1111 is located on the upper right arm
position recognition unit #2222 is located on the upper left arm
position recognition unit #3333 is located on the left foot
position recognition unit #4444 is located on the right foot Of course, the description of the locations may be specified more by using anatomical terms to indicate the precise bone or limb the position recognition unit is placed upon.

The next step involves placing a sensor onto the position recognition unit. By this it is ensured that the sensor attached correctly. Preferably, the sensor and the communication unit are integrated into each other. The communication unit then reads the unique identification of the sensor and the position recognition unit. This reading can be done via optical or electrical means, the latter further distinguished by wireless or wired transfer. A result could be:
position recognition unit #1111 is contacted by sensor #5555
position recognition unit #2222 is contacted by sensor #6666
position recognition unit #3333 is contacted by sensor #7777
position recognition unit #4444 is contacted by sensor #8888

The data pair of the unique identification of the position recognition unit and the sensor is then transmitted to the data processing unit by the communication unit. Again, this may be done via wired or wireless transfer. This data processing unit is in communication with a database where the data pairs of unique identification of the position recognition unit and its pre-determined position are stored. As the data processing unit now has all necessary information available, it can correlate the unique identifier of the sensor and with a pre-determined position. A result could be:
sensor #5555 is located on the upper right arm
sensor #6666 is located on the upper left arm
sensor #7777 is located on the left foot
sensor #8888 is located on the right foot From this it follows that the signals originating from the individual sensors can also be correlated with a pre-determined position.

In summary, the need to always place a certain sensor in a specified location is eliminated. Arbitrary sensors can be placed on the required positions. The method according to the present invention then takes care of assigning individual positions to the sensors so that their signals can be processed, displayed and interpreted correctly.

In an embodiment of the method according to the present invention the sensor is selected from the group comprising motion sensors, inertial sensors, acceleration sensors, gravity sensors, magnetic field sensors, body temperature sensors, pulse sensors, blood oxygen sensors, electromyographical sensors, electrocardiographical sensors and/or optical markings for visual tracking. The sensors and markings have already been discussed above.

The present invention is furthermore concerned with the use of a system according to the present invention for automatically recognizing the position of a sensor on a person's body.

BRIEF DESCRIPTION OF THE DRAWINGS

The present invention will become more readily understood with reference to the following drawing, wherein.

DETAILED DESCRIPTION OF THE EMBODIMENTS

Figure 1:
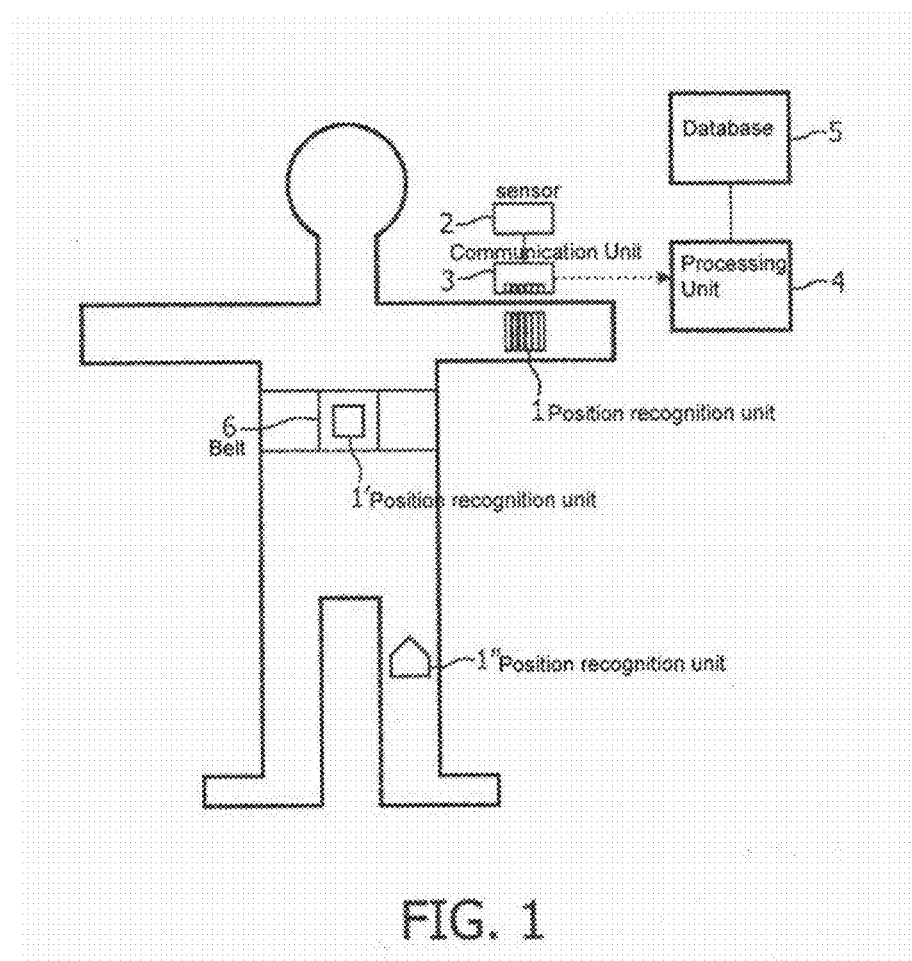
FIG. 1 shows a person with a system according to the present invention.

FIG. 1 schematically shows a person with a system according to the present invention. On one arm, the person bears optical marks in form of a bar code which constitute a position recognition unit (1). Furthermore, the person wears a second position recognition unit (1') inside a pocket of a belt (6) worn around the chest. By way of example, the person also bears a third position recognition unit (1") on his leg. This unit is shaped in such a way that it can be accessed in only one pre-determined orientation. The unique identification of each unit (1, 1', 1") as well as their location is stored in database (5).

Returning to the bar code position recognition unit (1), this is contacted by communication unit (3). The bar code contains a unique identification number encoded by means of varying the thickness of the lines. The communication unit (3) reads this bar code and extracts the unique identification. Furthermore, the communication unit reads the unique identification of the sensor (2). Communication unit (3) and sensor (2) form a distinct entity, in particular they are mechanically connected. The communication unit (3) transmits the gathered information to data processing unit (4), as indicated by the dashed arrow. This data processing unit (4) is in communication with database (5). Using the correlated data of unique identification/location of position recognition unit (1) and unique identification of sensor (2) and position recognition unit (1) the data processing unit (4) can then assign a location to sensor (2).

To provide a comprehensive disclosure without unduly lengthening the specification, the applicant hereby incorporates by reference each of the patents and patent applications referenced above.

The particular combinations of elements and features in the above detailed embodiments are exemplary only; the interchanging and substitution of these teachings with other teachings in this and the patents/applications incorporated by reference are also expressly contemplated. As those skilled in the art will recognize, variations, modifications, and other implementations of what is described herein can occur to those of ordinary skill in the art without departing from the spirit and the scope of the invention as claimed. Accordingly, the foregoing description is by way of example only and is not intended as limiting. The invention's scope is defined in the following claims and the equivalents thereto. Furthermore, reference signs used in the description and claims do not limit the scope of the invention as claimed.

The invention claimed is:

1. An automatic sensor position recognition system for recognizing pre-determined anatomical parts of a person's body, the system comprising:
   a position recognition unit bearing a first identification including a first unique identifier for placement at pre-determined anatomical parts of the person's body, the first unique identifier uniquely identifying the pre-determined part;
   a sensor uniquely identified by a second unique identifier and having a communication unit, the sensor is configured to
      detect a physiological condition of a person at a location of the sensor and the first unique identifier of the position recognition unit, and
      transmit the first and second unique identifiers and the detected physiological condition of the person; and
   a data processing unit configured to
      receive the first and second unique identifiers and the detected physiological condition of the person, and
      correlate the pre-determined position of the position recognition unit bearing the received first unique identifier with the location of the sensor bearing the received second unique identifier and the detected physiological condition of the person.

2. The system according to claim 1, wherein the first unique identifier is optically readable.

3. The system according to claim 1, wherein the first unique identifier is electrically readable.

4. The system according to claim 1, comprising a garment, wherein the position recognition unit is contained within a part of the garment and the garment is configured to position the position recognition unit at the corresponding intended pre-determined anatomical part when the garment is worn by the person.

5. The system according to claim 1, wherein the position recognition unit is located directly on and/or in the person's body.

6. The system according to claim 1, wherein the sensor is configured to read the position recognition unit in only one pre-defined spatial orientation of the sensor.

7. The system according to claim 1, wherein the sensor is selected from the group comprising motion sensors, inertial sensors, acceleration sensors, gravity sensors, magnetic field sensors, body temperature sensors, pulse sensors, blood oxygen sensors, electromyographical sensors, electrocardiographical sensors and/or optical markings for visual tracking.

8. The system according to claim 1, wherein the system automatically recognizes the position of the position recognizing units on a person's body.

9. A method for automatically recognizing pre-determined positions on a person's body, the method comprising acts of:
   providing a position recognition unit at a pre-determined anatomical parts of a person's body, the position recognition unit bearing a first unique identifier uniquely identifying the pre-determined part;
   a sensor bearing a second unique identifier and detecting a physiological condition of a person at a location of a sensor;
   transmitting the first and second unique identifiers and the detected physiological condition of the person; and
   a data processing unit
      receiving the transmitted first and second unique identifiers and the detected physiological condition of the person, and
      correlating the predetermined position of the position recognizing unit bearing the received first unique identifier with the location of the sensor bearing the received second unique identifier and the detected physiological condition of the person.

10. The method according to claim 9, wherein the sensor is selected from the group comprising motion sensors, inertial sensors, acceleration sensors, gravity sensors, magnetic field sensors, body temperature sensors, pulse sensors, blood oxygen sensors, electromyographical sensors, electrocardiographical sensors and/or optical markings for visual tracking.

11. The method according to claim 9, wherein the act of reading the first unique identifier comprises an act of enabling the sensor to read the first unique identifier borne by the position recognition units in only one pre-defined spatial orientation of the sensor.

12. The method according to claim 9, comprising an act of configuring a garment to position the position recognition unit at the corresponding intended pre-determined position when the garment is worn by the person.

* * * * *